| United States Patent [19]
Fabricius et al.

[11] Patent Number: 4,950,074
[45] Date of Patent: Aug. 21, 1990

[54] METHOD OF DETERMINING THE REFRACTIVE INDEX OF A SUBSTANCE AND APPARATUS THEREOF

[75] Inventors: Norbert Fabricius, Schönau; Helmut Oeste, Dortmund; Helga Götz, Bingen-Buedesh; Ludwig Roβ, Armsheim; Hans-Jürgen Guttmann, Wiesbaden; Jürgen Kluge, Dossenheim; Jörg Baumgart, Waghäusel; Charitos Efstathiou, Rüsselsheim, all of Fed. Rep. of Germany

[73] Assignee: IOT Entwicklungsgesellshaft für Integrierte Optik-Technologie mbH, Waghäusel-Kirrlach, Fed. Rep. of Germany

[21] Appl. No.: 346,523

[22] Filed: May 2, 1989

[30] Foreign Application Priority Data

May 2, 1988 [DE] Fed. Rep. of Germany ....... 3814844

[51] Int. Cl.$^5$ ...................... G01N 21/41; G01N 21/45
[52] U.S. Cl. ...................................... 356/133; 356/361
[58] Field of Search ........................ 356/128, 133, 361; 350/96.11

[56] References Cited

U.S. PATENT DOCUMENTS 4,815,843  3/1989  Tiefenthaler et al. ............... 356/128

FOREIGN PATENT DOCUMENTS 249772  9/1987  German Democratic Rep. .
226832  12/1984  Japan ................................... 356/128

OTHER PUBLICATIONS

Enokihara et al., *Applied Optics*, vol. 27, No. 1, Jan. 1, 1988, pp. 109–113.
"Integrated Optics: An Introduction", Stewart E. Miller, The Bell System Technical Journal, vol. 48, No. 7, pp. 2059–2069, (Sep. 1969).
Schott-Information, vol. 3, p. 29, FIG. 3, (1987).

*Primary Examiner*—F. L. Evans
*Attorney, Agent, or Firm*—Walter Ottesen

[57] ABSTRACT

The invention is directed to a method for determining the refractive index (n) of a substance wherein monochromatic light is conducted to a single-mode wave guide integrated into a substrate. The wave guide is brought into contact with the substance to be measured along a segment of predetermined length. In this way, the effective refractive index in this segment of the wave guide is changed. This effect is utilized for measuring the refractive index of the measured substance. The change of the effective refractive index causes a phase displacement of the light travelling through this measuring segment. This phase displacement is measured as a phase difference to a light component not influenced by the measuring substance. This measurement is preferably made interferometrically.

13 Claims, 3 Drawing Sheets

4,950,074

METHOD OF DETERMINING THE REFRACTIVE INDEX OF A SUBSTANCE AND APPARATUS THEREOF

FIELD OF THE INVENTION

The invention relates to a method for determining the refractive index of a substance as well as an apparatus for carrying out the method.

BACKGROUND OF THE INVENTION

Optical instruments for determining the index of refraction (n) of a substance have long been known under the designation refractometer. In these classical optical apparatus, the determination of the refractive index preferably occurs by measuring the critical angle of the total reflection by utilizing a measurement prism having a known refractive index.

So-called interference refractometers are also known wherein the determination of the refractive index occurs with the aid of interferometric means. In the known apparatus, the detection of the measured value occurs visually or also by means of complex electronics.

All of these known apparatus comprise individual optical parts of high quality and require much space. The highest precision which is required for the manufacture of the optical and precision-mechanical components as well as the electronic evaluation and automatic apparatus make the cost thereof high.

Accordingly, the foregoing has resulted in a desire amongst engineers and technicians for substantially smaller, simpler and more portable apparatus at a lower cost.

An interesting and promising path toward miniaturization of optical instruments was presented already in 1969 in the technical paper entitled "Integrated Optics: an introduction" by Stewart E. Miller, the Bell System Technical Journal, Volume 48, No. 7, pages 2059 to 2069, September 1969. The suggestions made in this paper with regard to the assembly and utilization of integrated optical components were however not realizable because of technical reasons.

Only after an intensive technological development in the area of materials and mask technology could substantial advances be obtained in the realization of integrated optical components during the past several years. Suitable substrate materials made of glass, crystalline substances or transparent plastics were developed in which wave guides of suitable configuration could be integrated by means of ion diffusion, ion implantation or by means of applying organic or metal-organic layers.

As a consequence of the foregoing, integrated-optical components have been developed which have taken over the following tasks in transmission systems: modulation, switching, interconnecting channels, branching and the like. Even apparatus for measuring physical quantities have become known wherein integrated-optical components are used as sensors.

In the publication "Schott-Information", Volume 3, page 29, FIG. 3, (1987), an integrated-optical hydrogen sensor is shown. An integrated-optical temperature sensor is described in East German Pat. No. 249,772 wherein the sensor has an interferometer configuration wherein temperature-dependent changes of the phase difference between the light running through both interferometer branches is utilized for measuring temperature.

SUMMARY OF THE INVENTION

In view of the foregoing, it is an object of the invention to provide a method for determining the index of refraction (n) of a substance which delivers highly precise results in an especially simple manner. It is another object of the invention to provide an apparatus for carrying out the invention which is cost-effective, small and simple to handle.

The method of the invention is for determining the index of refraction (n) of a substance. The method includes the steps of: conducting monochromatic light to an optical single-mode wave guide integrated into a substrate, the wave guide having a measurement segment of predetermined length and an effective refractive index along said segment; bringing the substance to be measured into optical contact with the wave guide along said measurement segment thereby changing the effective refractive index of the wave guide along said segment; and, determining the refractive index (n) from the change in said effective refractive index.

The invention is based on the premise that the wave travelling through the wave guide and through the measuring segment which is a part of the wave guide comes into optical contact with the substance to be measured. It is along this measuring segment that the light also travels partially through the substance to be measured. In this way, the velocity of propagation and thereby also the effective refractive index in the wave guide is changed.

This change of the effective refractive index leads to a phase change of the light passing through the wave guide. This phase change is measured as the difference to the phase of a light component which is not influenced. This measurement occurs preferably interferometrically.

The change of the effective refractive index in the wave guide also leads to the condition that the polarization direction of a polarized light passing through the measuring segment is changed in dependence upon the refractive index of the substance to be measured. For making the measurement, a signal can, for example, be utilized which cancels the change in the direction of polarization.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
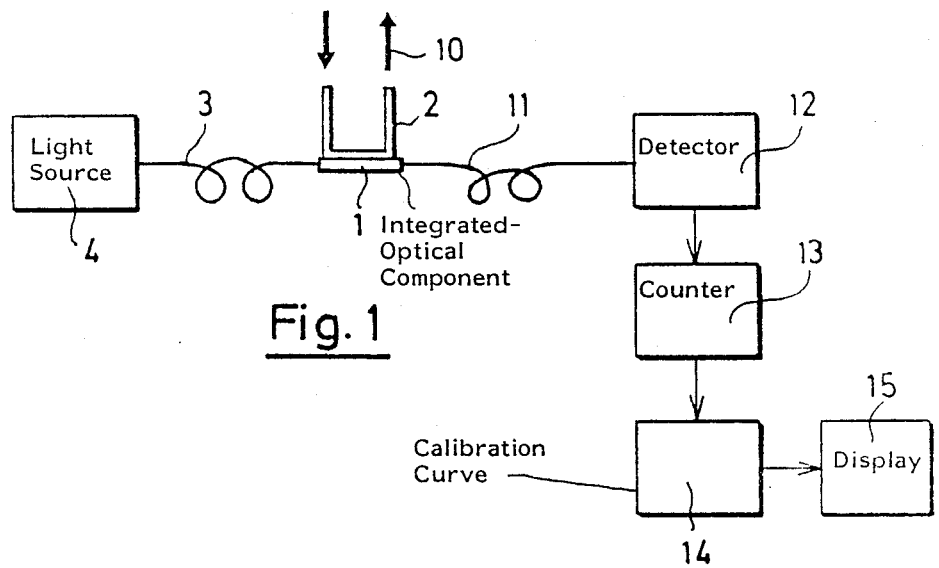
FIG. 1 is a schematic of an embodiment of the apparatus according to the invention wherein the index of refraction (n) of a substance is determined by interferometric means.

In the embodiments shown in the drawings, glass is used as a substrate which is produced under the designation BGG 21 and is commercially available from the Schott Glaswerke, an institution organized and doing business in the Federal Republic of Germany. The characteristics of this glass are delineated on page 27 of the article referred to above which appears in the publication "Schott-Information". Strip-like wave guides are integrated into this substrate.

Figure 3:
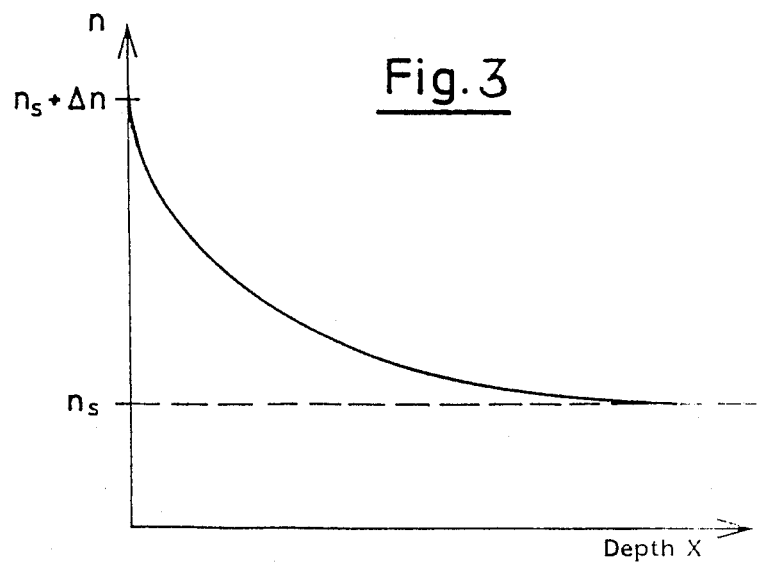
FIG. 3 shows a curve representing the refractive index profile of the wave guide of the integrated-optical component of FIG. 2 with the wave guide being produced by means of a thermal ion exchange.

To produce these wave guides, a mask is generated on the substrate according to known planar technology which leaves only the region of the wave guide exposed. The substrate prepared in this manner is introduced into a hot salt solution of $CsNO_3/CsCl$ at a temperature of 410° C. for several hours. A thermal ion exchange then takes place by means of which the $Cs^+$-ions migrate into the substrate and the $K^+$-ions migrate out of the substrate. In this way, a wave guide is produced in the substrate having the refractive index $n_s$. This wave guide has a refractive index profile measured perpendicularly to the surface which has the form shown in FIG. 3, for example. From this curve, it can be recognized that the refractive index at the surface has the value $(n_s + \Delta n)$ and that this value drops down again to the value $n_s$ at the opposite-lying boundary surface of the wave guide which is determined by the depth of diffusion. This wave guide has a specific refractive index $n_{eff}$ assigned to the light wave for the mode of the light travelling in the wave guide and having the wave length $\lambda_0$. The following condition applies for the foregoing: $n_s < n_{eff} < (n_s + \Delta n)$.

The ion exchange is conducted so that single mode wave guides are produced. In the wavelength range of 400–1600 nm, such a wave guide has a base attenuation of less than 0.1 dB/cm. The diffusion depth for such a wave guide lies in the range of approximately 1.5 μm to 10 μm.

In the embodiment of FIG. 1, reference numeral 1 designates an integrated-optical component whose configuration and operation will be more carefully explained in connection with FIG. 2. A single-mode light-conducting fiber 3 is cemented to the light entrance end. This light-conducting fiber 3 conducts the light emanating from a monochromatic light source 4 to the component 1. A laser can be utilized as a suitable light source which operates at a wavelength of $\lambda_0 = 633$ nm for the embodiment shown.

A through-flow cuvette 2 is placed on the integrated-optical component 1 through which the substance 10 to be measured flows. As will be shown in the following, this substance is partially in optical contact with the one or more wave guides of the component 1 and thereby effects a phase change of the light coupled in via the fiber 3. A further single-mode light-conducting fiber 11 is cemented to the light exit end of the integrated-optical component 1. This light-conducting fiber 11 conducts the light influenced by the measuring substance to a detector 12. In the simplest case, the phase change of the light effected by the measuring substance 10 is determined by a measurement of the intensity change which occurs as soon as the measuring substance 10 is brought into optical contact to the wave guide of the component 1.

In the embodiment of FIG. 1, the detector 12 is connected to a counter 13 which, for example, counts the interference maxima in the signal. By means of a comparison with a calibration curve stored in element 14, the phase change of the light detected by the counter 13 is converted into the n-value of the index of refraction and indicated on the display 15.

Figure 2:
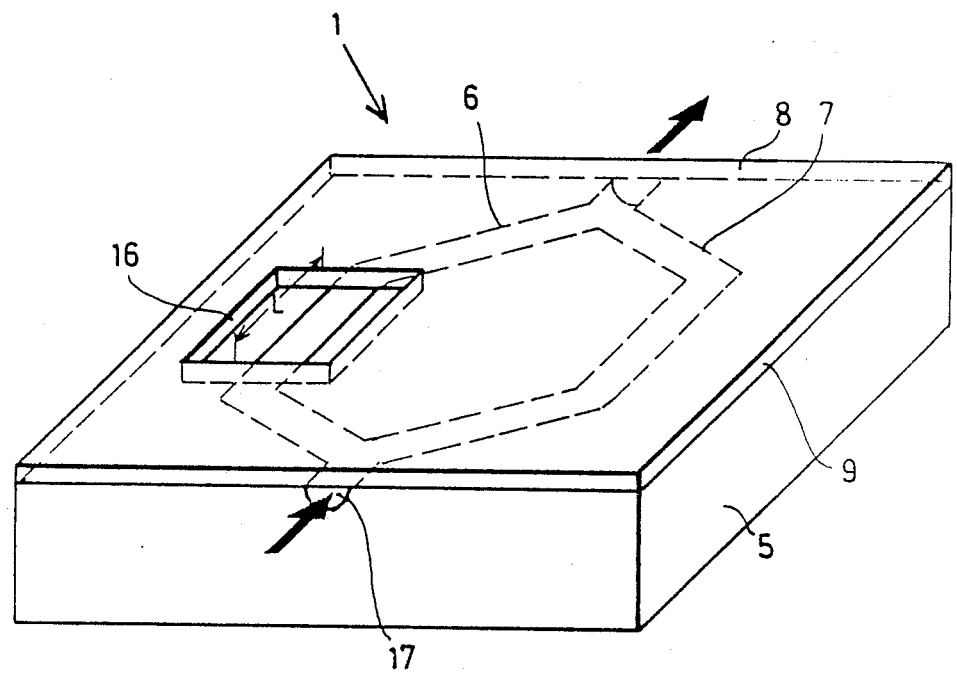
FIG. 2 is a perspective view of the integrated-optical component functioning as a sensor in FIG. 1.

FIG. 2 is a perspective view of the integrated-optical component identified in FIG. 1 by reference numeral 1. A wave guide is integrated with the substrate 5 and light is conducted to this wave guide at its light entrance end 17 from the light source 4 via the single-mode light-conducting fiber 3. The wavelength of this light is so selected that the light-conducting fibers and wave guides utilized have a single mode.

The wave guide integrated into the substrate 5 has the form of a Mach-Zehnder interferometer structure. It branches into the two arms (6, 7) which are rejoined at the light exit end. A covering layer 9 is applied to the substrate 5 and is made of a material having a refractive index which is equal to or less than the refractive index of the substrate 5. This layer can, for example, be made of polyvinylidene fluoride having an index of refraction $n = 1.42$. The cover layer 9 does not cover the arm 6 of the wave guide over a region 16 having the length (L). The substance 10 to be measured can, for example, be a liquid which is brought onto the layer 9 by means of the through-flow cuvette 2 and thereby comes into optical contact with the wave guide in the measuring arm 6 over the region 16. The light wave conducted in via the fiber 3 travels also partially in the measuring substance 10. In this way, the velocity of propagation of the light in the arm 6 and thereby also the phase of this light is influenced. The phase of the light travelling via the reference arm 7 is virtually uninfluenced since the refractive index of the layer is equal to or less than the refractive index of the substrate 5. The two light components conducted via the arms (6, 7) interfere after being joined at the light exit end 8.

Figure 4:
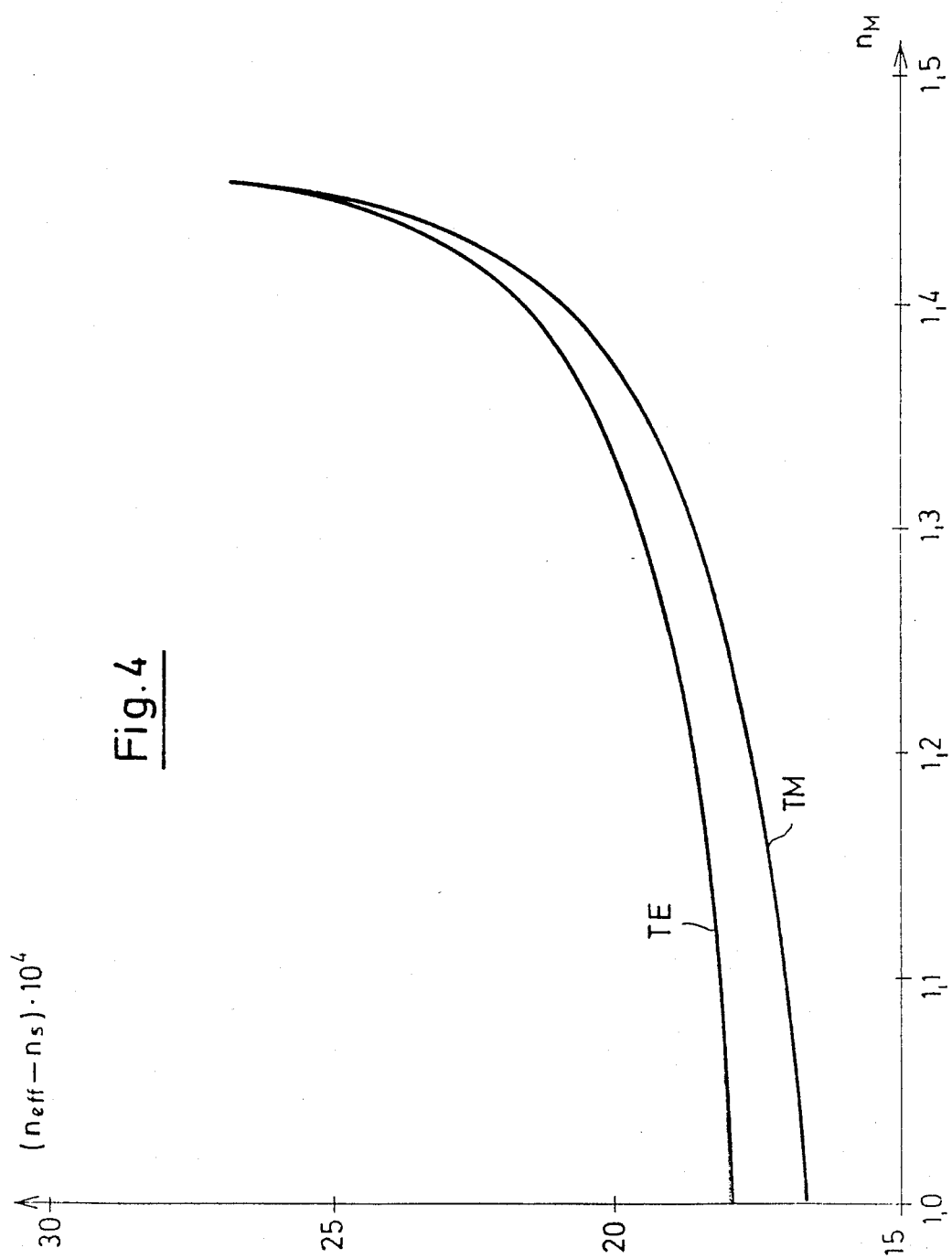
FIG. 4 is a calibration curve for determining the refractive index of the substance with the apparatus of FIG. 1; and, FIG. 5 is another embodiment of an apparatus of the invention for determining the index of refraction (n) of a substance wherein this determination is made by measuring the change in the direction of polarization of the light travelling through the wave guide.

The optical contact of the measuring arm 6 with the measuring substance 10 changes the effective refractive index $n_{eff}$ of the wave guide over the region (L). The connection between the refractive index $n_M$ of the medium to be measured and the effective refractive index of the wave guide is illustrated in FIG. 4 for the TM-mode and TE-mode which are polarized perpendicularly to each other. In this illustration, the ordinate (n) indicates the value $(n_{eff} - n_s) \cdot 10^4$. The curves of FIG. 4 can be either or they can be determined by measurement. The curves of FIG. 4 are stored as calibration curves in element 14.

From the curves of FIG. 4, it can be recognized that a definite connection results between the effective refractive index $n_{eff}$ of the light conductor and the refractive index $n_M$ of the measured substance. In the embodiment shown, the usable measuring range for values of $n_M$ lies in the range of 1.2 to 1.46.

The change of the effective refractive index $n_{eff}$ in the region of the measuring arm 6 leads to a phase displacement of the light travelling through this arm, this phase displacement being proportional to the contact length (L). A comparison of the phase of the light in the measuring arm 6 with the phase in the reference arm 7 provides a phase difference $\Delta\phi$ which is a measure for the refractive index $n_M$ which is sought pursuant to the formula:

$$\Delta\phi = \frac{2\pi L}{\lambda_0} \cdot \Delta n_{eff}(n_m)$$

wherein: $\Delta n_{eff}$ is the difference of the effective refractive indices in the two arms (6, 7) of the integrated-optical component 1.

The phase difference $\Delta\phi$ leads to an interference of the light waves travelling via the arms (6, 7). The interference signal is conducted to the detector 12 via the light-conducting fiber 11 and is converted via the electronic components (13, 14) into an $n_M$-signal which is indicated on the display 15.

In the embodiment of FIG. 2, the length L of the contact region is 1 cm. The lateral spacing between the two arms (6, 7) of the integrated optical component 1 lies in the order of magnitude of 1 mm. This affords the advantage that the local temperature effects average and the element 1 exhibits only a negligibly small transverse sensitivity.

The integrated-optical refractive index sensor of FIG. 1 can be advantageously used in the sugar industry for measuring the sugar concentration. An especially advantageous application is provided in the petrochemical industry since the refractive index sensor causes no problems with respect to protection against explosion.

Glass was described as a substrate material in connection with the embodiments described above. However, other substrate materials are possible in dependence upon the area of utilization such as crystalline substances, for example: $LiNbO_3$, $LiTaO_3$, GaAs, InP and/or mixed compounds thereof. Transparent plastics are also usable as a substrate material. All substrate materials must make possible the production of wave guide structures according to the known processes which exhibit a low attenuation for the operating wavelength. The selection of the suitable substrate material can occur pursuant to other viewpoints and also according to the requirement that the refractive $n_s$ is only slightly higher than the particular refractive index measuring range of the sensor.

In organic chemistry, the refractive indices $n_M$ of the substances to be measured lie in the range of approximately 1.2 to 1.5. For these measuring ranges too, suitable substrate materials can be found among the compounds discussed above.

The measuring process and the measuring apparatus remain unchanged independently of the material utilized.

In the embodiment of FIGS. 1 and 2, the integrated-optical component 1 is configured in the form of an interferometer. Other embodiments are possible which make possible the measurement of the phase difference $\Delta\phi$.

Figure 5:
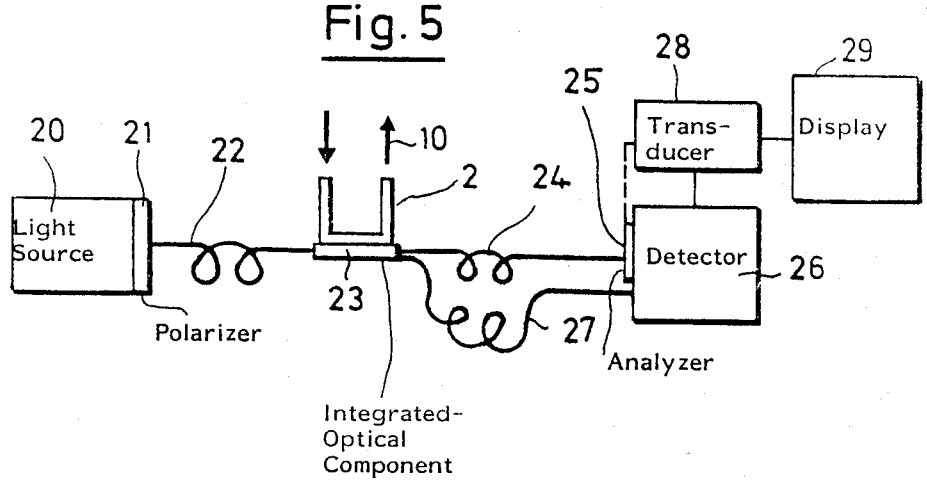

A further embodiment which operates pursuant to another principle is shown in FIG. 5.

In the embodiment of FIG. 5, the change of the polarization direction of light from the light source is utilized for making measurements. The light generated by a monochromatic light source 20 travels through a polarizer 21 and is conducted via the light-conducting fiber 22 to an integrated-optical component 23. At the light entrance end, this component 23 includes a light conductor branced into two arms which run parallel to each other. As in FIG. 2, one of these arms is so configured that the measuring substance 10 is in direct optical contact with the wave guide along the length (L). In this way, the polarization plane of the light is rotated.

The light travelling through this arm is conducted by a light-conducting fiber 24 via an analyzer 25 to a detector 26. The light in the other arm of the component 23, which is not influenced, reaches the detector 26 via a separate light conductor 27. This detector 26 determines the rotation of the polarization plane and generates a signal via the element 28 which rotates the analyzer 25 until the rotation of the polarization plane is precisely compensated. This signal is displayed on the display 29.

It is understood that the foregoing description is that of the preferred embodiments of the invention and that various changes and modifications may be made thereto without departing from the spirit and scope of the invention as defined in the appended claims.

What is claimed is:

1. A method of determining the index of refraction (n) of a substance, the method comprising the steps of:
   conducting monochromatic light to an optical single-mode wave guide integrated into a substrate; the wave guide defining two paths for conducting respective components of light therealong; one of said paths having a measurement segment of predetermined length (L) and an effective refractive index along said segment;
   bringing the substance to be measured into optical contact with the wave guide along said measurement segment thereby changing the effective refractive index of the wave guide along said segment to produce a phase displacement of the light travelling along the path of said measurement segment; and,
   determining the refractive index (n) from the phase difference between the components of light travelling along said two light paths.

2. The method of claim 1, wherein the measurement of said index of refraction (n) is performed interferometrically.

3. A method of determining the index of refraction (n) of a substance, the method comprising the steps of:
   conducting monochromatic light to an optical single-mode wave guide integrated into a substrate, the wave guide having a measurement segment of predetermined length (L) and an effective refractive index along said segment; said light conducted to said wave guide being polarized light having a predetermined direction of polarization which changes in the measuring segment;
   bringing the substance to be measured into optical contact with the wave guide along said measurement segment thereby changing the effective refractive index of the wave guide along said segment; and,
   measuring the refractive index (n) from the change in said effective refractive index by utilizing the change in said direction.

4. Apparatus for determining the index of refraction ($n_M$) of a substance, the apparatus comprising:
   a monochromatic light source for producing a monochromatic light;
   a substrate having an optical single-mode wave guide integrated therein;
   said wave guide having a light entrance end for receiving said monochromatic light and a light exit end whereat the light travelling through said wave guide exits therefrom;

said wave guide having two arms dividing at said light entrance end into said two arms which are rejoined at said light exit end;

said wave guide having a measuring segment of a predetermined length (L) provided on one of said arms;

a cover layer formed on said substrate so as to cover said wave guide except for said measuring segment;

means for bringing said substance into optical contact with said measuring segment; and, a detector arrangement for receiving the light from said light exit end and converting the same into a signal proportional to the index of refraction (n) of said substance.

5. The apparatus of claim 4, said wave guide being a first strip-shaped optical single-mode wave guide integrated in said substrate and said apparatus further comprising a second strip-shaped optical single-mode wave guide likewise integrated in said substrate; said wave guides being parallel to each other and configured so as to evenly divide the light from said light source; and, said measuring segment being provided only on said first wave guide.

6. The apparatus of claim 4, said substrate having a predetermined index of refraction; and, said cover layer having an index of refraction equal to or less than the index of refraction of said substrate.

7. The apparatus of claim 6, said cover layer being made of polyvinylidene fluoride.

8. Apparatus for determining the index of refraction ($n_M$) of a substance, the apparatus comprising:

a monochromatic light source for producing a monochromatic light;

a substrate having an optical single-mode wave guide integrated therein;

said wave guide having a light entrance end for receiving said monochromatic light and a light exit end whereat the light travelling through said wave guide exits therefrom and said wave guide having a measuring segment of a predetermined length (L);

means for bringing said substance into optical contact with said measuring segment;

a detector arrangement for receiving the light from said light exit end and converting the same into a signal proportional to the index of refraction (n) of said substance;· said wave guide being a first strip-shaped optical single-mode wave guide integrated in said substrate;

a second strip-shaped optical single-mode wave guide likewise integrated in said substrate;

said wave guides being parallel to each other and configured so as to evenly divide the light from said light source; and, said measuring segment being provided only on said first wave guide.

9. Apparatus for determining the index of refraction ($n_M$) of a substance, the apparatus comprising:

a monochromatic light source for producing a monochromatic light;

a substrate having an optical single-mode wave guide integrated therein;

said wave guide having a light entrance end for receiving said monochromatic light and a light exit end whereat the light travelling through said wave guide exits therefrom and said wave guide having a measuring segment of a predetermined length (L);

means for bringing said substance into optical contact with said measuring segment;

a detector arrangement for receiving the light from said light exit end and converting the same into a signal proportional to the index of refraction (n) of said substance;

said wave guide having two arms dividing at said light entrance end into said two arms which are rejoined at said light exit end; and, said measuring segment being provided on only one of said two arms.

10. The apparatus of claim 9, said substrate having a predetermined index of refraction; said apparatus further comprising a cover layer formed on said substrate so as to cover said wave guide except for said measuring segment; and, said cover layer having an index of refraction equal to or less than the index of refraction of said substrate.

11. The apparatus of claim 10, said cover layer being made of polyvinylidene fluoride.

12. Apparatus for determining the index of refraction ($n_M$) of a substance, the apparatus comprising:

a monochromatic light source for producing a monochromatic light;

polarization means for polarizing the light from said light source;

a substrate having an optical single-mode wave guide integrated therein;

said wave guide having a light entrance end for receiving the polarized monochromatic light;

said wave guide including two arms formed in said substrate so as to communicate with said light entrance end for conducting respective components of light;

measurement segment means formed in said substrate along one of said two arms to facilitate optical contact with said one arm;

means for bringing said substance into optical contact with said one arm via said measurement segment means thereby rotating the polarization plane of the light component travelling through said one arm;

said arms terminating in respective light exits through which said light components exit from said wave guide; and, detector means for receiving said light components and for determining the rotation of the polarization plane as an indication of the index of refraction ($n_M$) of the substance.

13. The apparatus of claim 12, comprising means for measuring the index of refraction ($n_M$) by compensating for the rotation of said polarization plane.

* * * * *

UNITED STATES PATENT AND TRADEMARK OFFICE
CERTIFICATE OF CORRECTION

PATENT NO. : 4,950,074
DATED : August 21, 1990
INVENTOR(S) : Norbert Fabricius, Helmut Oeste, Helga Götz, Ludwig Ross, Hans-Jürgen Guttmann, Jürgen Kluge, Jörg Baumgart and Charitos Efstathiou It is certified that error appears in the above-identified patent and that said Letters Patent is hereby corrected as shown below:

On the title page, in the title, line 3: delete "THEREOF" and substitute -- THEREFOR --.

In column 1, line 3 of the title: delete "THEREOF" and substitute -- THEREFOR --.

In column 4, line 50: insert -- computed -- between "either" and "or".

In column 5, in the formula: delete "$(n_m)$" and substitute -- $n_M$ -- therefor.

In column 5, line 39: insert -- index -- after "refractive".

In column 5, line 64: delete "branced" and substitute -- branched -- therefor.

Signed and Sealed this

Fourteenth Day of January, 1992

Attest:

HARRY F. MANBECK, JR.

*Attesting Officer*   *Commissioner of Patents and Trademarks*